US009585608B2

(12) United States Patent
Valdes et al.

(10) Patent No.: US 9,585,608 B2
(45) Date of Patent: Mar. 7, 2017

(54) CONTINUOUS ANALYTE MONITOR DATA RECORDING DEVICE OPERABLE IN A BLINDED MODE

(71) Applicant: DexCom, Inc., San Diego, CA (US)

(72) Inventors: Jorge Valdes, San Diego, CA (US); David Price, Carlsbad, CA (US); Leif N. Bowman, Livermore, CA (US); Kristin Cote, Oakland, CA (US)

(73) Assignee: DexCom, Inc., San Diego, CA (US)

( * ) Notice: Subject to any disclaimer, the term of this patent is extended or adjusted under 35 U.S.C. 154(b) by 3 days.

(21) Appl. No.: 14/938,712

(22) Filed: Nov. 11, 2015

(65) Prior Publication Data

US 2016/0058353 A1 Mar. 3, 2016

Related U.S. Application Data

(63) Continuation of application No. 13/282,182, filed on Oct. 26, 2011, now Pat. No. 9,241,631.

(Continued)

(51) Int. Cl.
| | |
|---|---|
| *A61B 5/05* | (2006.01) |
| *A61B 5/1486* | (2006.01) |
| *A61B 5/00* | (2006.01) |
| *A61B 5/15* | (2006.01) |
| *A61B 5/155* | (2006.01) |
| *A61B 5/145* | (2006.01) |
| *A61B 5/151* | (2006.01) |
| *A61B 5/157* | (2006.01) |
| *A61B 5/1473* | (2006.01) |
| *A61B 5/1495* | (2006.01) |

(52) U.S. Cl.
CPC ........ *A61B 5/14865* (2013.01); *A61B 5/0004* (2013.01); *A61B 5/0022* (2013.01);
(Continued)

(58) Field of Classification Search
CPC .............. A61B 5/14735; A61B 5/1495; A61B 2562/0295; A61B 5/0024; A61B 5/1486; A61B 5/00; A61B 5/145; A61B 5/155; A61B 5/157; A61B 5/746; A61B 5/0004; A61B 5/14546; A61B 5/14865; A61B 5/7282; A61B 5/0022; A61B 5/742; A61B 5/1411; A61B 5/1427; A61B 5/14532; A61B 5/150022; A61B 5/150267; A61B 5/150358; A61B 5/150854; A61B 5/150862; A61B 5/15087; A61B 5/150877; A61B 5/150969; A61B 5/15105
See application file for complete search history.

(56) References Cited

U.S. PATENT DOCUMENTS

| 5,507,288 A | 4/1996 | Bocker et al. |
| 5,665,065 A | 9/1997 | Colman et al. |
(Continued)

FOREIGN PATENT DOCUMENTS

| WO | WO 96/37246 | 11/1996 |
| WO | WO 97/01986 | 1/1997 |

*Primary Examiner* — Navin Natnithithadha
*Assistant Examiner* — Eric Messersmith
(74) *Attorney, Agent, or Firm* — Knobbe Martens Olson & Bear, LLP

(57) ABSTRACT

A system is provided for monitoring analyte in a host, including a continuous analyte sensor that produces a data stream indicative of a host's analyte concentration and a device that receives and records data from the data stream from the continuous analyte sensor. In one embodiment, the device includes a single point analyte monitor, from which it obtains an analyte value, and is configured to display only single point analyte measurement values, and not any analyte measurement values associated with data received from the continuous analyte sensor. Instead, data received from the continuous analyte sensor is used to provide alarms to the user when the analyte concentration and/or the rate of change of analyte concentration, as measured by the continuous analyte sensor, is above or below a predetermined range. Data received from the continuous analyte sensor may also be used to prompt the diabetic or caregiver to take certain actions, such as to perform another single point blood glucose measurement. In another embodiment, the device provides for toggling between two modes, with one mode that allows for display of glucose concentration values associated with the continuous glucose sensor and a second mode that prevents the display of glucose concentration values associated with the continuous glucose sensor.

20 Claims, 7 Drawing Sheets

Related U.S. Application Data

(60) Provisional application No. 61/407,412, filed on Oct. 27, 2010.

(52) U.S. Cl.
CPC .......... *A61B 5/1411* (2013.01); *A61B 5/1427* (2013.01); *A61B 5/14532* (2013.01); *A61B 5/14546* (2013.01); *A61B 5/155* (2013.01); *A61B 5/157* (2013.01); *A61B 5/150022* (2013.01); *A61B 5/15087* (2013.01); *A61B 5/15105* (2013.01); *A61B 5/150267* (2013.01); *A61B 5/150358* (2013.01); *A61B 5/150854* (2013.01); *A61B 5/150862* (2013.01); *A61B 5/150877* (2013.01); *A61B 5/150969* (2013.01); *A61B 5/7282* (2013.01); *A61B 5/742* (2013.01); *A61B 5/746* (2013.01); *A61B 5/0024* (2013.01); *A61B 5/1495* (2013.01); *A61B 5/14735* (2013.01); *A61B 2562/0295* (2013.01)

(56) References Cited

U.S. PATENT DOCUMENTS

| | | |
|---|---|---|
| 5,772,586 A | 6/1998 | Heinonen et al. |
| 5,899,855 A | 5/1999 | Brown |
| 5,995,860 A | 11/1999 | Sun et al. |
| 6,396,416 B1 | 5/2002 | Kuusela et al. |
| 6,428,475 B1 | 8/2002 | Shen |
| 6,494,830 B1 | 12/2002 | Wessel |
| 6,558,320 B1 | 5/2003 | Causey et al. |
| 6,571,128 B2 | 5/2003 | Lebel et al. |
| 6,641,533 B2 | 11/2003 | Causey et al. |
| 6,699,188 B2 | 3/2004 | Wessel |
| 6,958,705 B2 | 10/2005 | Lebel et al. |
| 7,299,082 B2 | 11/2007 | Feldman et al. |
| 7,447,596 B2 | 11/2008 | Kawatahara et al. |
| 7,519,408 B2 | 4/2009 | Rasdal et al. |
| 7,587,287 B2 | 9/2009 | Connolly et al. |
| 7,591,801 B2 | 9/2009 | Brauker et al. |
| 7,595,723 B2 | 9/2009 | Heitzmann et al. |
| 7,602,310 B2 | 10/2009 | Mann et al. |
| 7,722,536 B2 | 5/2010 | Goodnow |
| 7,927,274 B2 | 4/2011 | Rasdal et al. |
| 7,976,492 B2 | 7/2011 | Brauker et al. |
| 8,029,459 B2 | 10/2011 | Rush et al. |
| 8,029,460 B2 | 10/2011 | Rush et al. |
| 2003/0208113 A1 | 11/2003 | Mault et al. |
| 2007/0244383 A1 | 10/2007 | Talbot et al. |
| 2008/0228057 A1 | 9/2008 | Graskov et al. |
| 2008/0287761 A1 | 11/2008 | Hayter et al. |
| 2008/0287765 A1 | 11/2008 | Rasdal et al. |
| 2008/0319295 A1 | 12/2008 | Bernstein et al. |
| 2009/0069655 A1 | 3/2009 | Say et al. |
| 2009/0131860 A1 | 5/2009 | Nielsen |
| 2010/0137698 A1 | 6/2010 | Andrews et al. |

CONTINUOUS ANALYTE MONITOR DATA RECORDING DEVICE OPERABLE IN A BLINDED MODE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/282,182, filed on Oct. 26, 2011, which claims the benefit of U.S. Provisional Application 61/407,412, filed on Oct. 27, 2010. Each of the aforementioned applications is incorporated by reference herein in its entirety, and each is hereby expressly made a part of this specification.

FIELD OF THE INVENTION

The embodiments described herein relate generally to a system including a continuous analyte sensor and a device configured to communicate with and record data from the continuous analyte sensor, and to provide a single point analyte measurement.

BACKGROUND OF THE INVENTION

Diabetes mellitus is a chronic disease, which occurs when the pancreas does not produce enough insulin (Type I), or when the body cannot effectively use the insulin it produces (Type II). This condition typically leads to an increased concentration of glucose in the blood (hyperglycemia), which can cause an array of physiological derangements (e.g., kidney failure, skin ulcers, or bleeding into the vitreous of the eye) associated with the deterioration of small blood vessels. Sometimes, a hypoglycemic reaction (low blood sugar) is induced by an inadvertent overdose of insulin, or after a normal dose of insulin or glucose-lowering agent accompanied by extraordinary exercise or insufficient food intake.

People with type 1 diabetes generally have to submit to a demanding daily regimen that typically requires frequent monitoring of blood glucose (BG) and dosing of insulin by injection or infusion pump, in order to maintain safe blood sugar levels. Under current FDA regulations, a diabetic or caregiver can not make dosing decisions off of conventional continuous glucose monitoring (CGM) technology. Accordingly, even with the use of a conventional CGM system, the diabetic or a caregiver would still be required to double-check glucose levels by using a blood glucose monitoring (BGM) device, in determining whether to administer insulin. Use of BGM devices traditionally involves pricking of a finger to obtain a small blood sample, which the diabetic or caregiver applies onto a strip that is inserted in the BGM device.

SUMMARY OF THE INVENTION

In a first aspect, a system for monitoring glucose concentration is provided, the system comprising: a continuous glucose sensor, the continuous glucose sensor configured to continuously measure glucose concentration and output a data stream associated with glucose concentration; and a device configured to operatively connect with the continuous glucose sensor, the device comprising a single point glucose monitor, at least one processor configured to process the data stream from the continuous glucose sensor, and a user interface configured to display measured glucose concentration values associated with the single point glucose monitor.

In an embodiment of the first aspect, the device is configured to not display glucose concentration values associated with the data stream from the continuous glucose sensor.

In an embodiment of the first aspect, the device is configured for toggling between a first mode allowing for display of glucose concentration values associated with the continuous glucose sensor and a second mode preventing display of glucose concentration values associated with the continuous glucose sensor.

In an embodiment of the first aspect, the at least one processor is configured to determine when to trigger an alarm, wherein the determination of when to trigger the alarm is based at least in part on information associated with the processed data stream.

In an embodiment of the first aspect, the alarm is configured to warn a user of a pending hyperglycemic event or a pending hypoglycemic event.

In an embodiment of the first aspect, the at least one processor is configured to determine when to prompt a user to perform a single point glucose measurement, wherein the determination of when to prompt the user is based at least in part on information associated with the processed data stream.

In an embodiment of the first aspect, the continuous glucose sensor is an implantable device.

In an embodiment of the first aspect, the single point glucose monitor is configured to measure a glucose concentration in blood.

In an embodiment of the first aspect, the device further comprises a memory for recording at least one of the data stream from the continuous analyte sensor or measured glucose concentration values associated with the single point glucose monitor.

In a second aspect, a system for monitoring glucose concentration is provided, the system comprising: a continuous glucose sensor, the continuous glucose sensor configured to continuously measure glucose concentration and output a data stream associated with glucose concentration; and a device configured to operatively connect with the continuous glucose sensor, the device comprising a single point glucose monitor, at least one processor configured to process the data stream from the continuous glucose sensor, the at least one processor configured to determine when to prompt a user to perform a single point glucose measurement, wherein the determination of when to prompt the user is based at least in part on information associated with the processed data stream.

In an embodiment of the second aspect, the device is configured to display glucose concentration values associated with the single point glucose monitor.

In an embodiment of the second aspect, the device is configured for toggling between a first mode allowing for display of glucose concentration values associated with the continuous glucose sensor and a second mode preventing display of glucose concentration values associated with the continuous glucose sensor.

In an embodiment of the second aspect, the device is configured to not display glucose concentration values associated with the data stream from the continuous glucose sensor.

In an embodiment of the second aspect, the at least one processor is further configured to determine when to trigger an alarm, wherein the determination of when to trigger the alarm is based at least in part on information associated with the processed data stream.

In an embodiment of the second aspect, the alarm is configured to warn a user of a pending hyperglycemic event or a pending hypoglycemic event.

In an embodiment of the second aspect, the continuous glucose sensor is an implantable device.

In an embodiment of the second aspect, the single point glucose monitor is configured to measure a glucose concentration in blood.

In an embodiment of the second aspect, the device further comprises a memory for recording at least one of the data stream from the continuous analyte sensor or measured glucose concentration values associated with the single point glucose monitor.

In a third aspect, a method for analyzing glucose concentration in a user is provided, the method comprising: receiving, from a continuous glucose sensor to a single point glucose monitor, a data stream associated with glucose concentration; processing the data stream; recording the data stream; determining when to trigger an alarm, wherein the determining of when to trigger the alarm is based at least in part on information associated with the processed data stream; and determining when to prompt a user to perform a single point glucose measurement, wherein the determining of when to perform the single point glucose measurement is based at least in part on information associated with the processed data stream.

In an embodiment of the third aspect, the method further comprises transferring the data stream from the single point glucose monitor to a device.

In an embodiment of the third aspect, the method further comprises performing retrospective analysis on the data stream on the device.

In a fourth aspect, a method for monitoring glucose concentration in a user comprises receiving, from a continuous analyte sensor, a data stream associated with analyte concentration, processing the data stream, recording the data stream without displaying any information associated with or derived from the data stream, and triggering an alarm based at least in part on information associated with the processed data stream.

In one embodiment of the fourth aspect, the alarm comprises a prompt to a user to perform a single point glucose measurement.

In another embodiment of the fourth aspect, the alarm comprises a notification of a hypoglycemic or hyperglycemic event.

In a fifth aspect, a system for continuous monitoring of an analyte concentration in a host comprises a continuous analyte sensor and a recording device configured to receive a data stream representative of analyte concentration in the host. The recording device is configurable to operate in a mode that restricts host access to data from the continuous analyte sensor while still providing alarms to the host based on data from the continuous analyte sensor.

In an embodiment of the fifth aspect, the recording device is configurable to operate in a second mode that allows host access to data from the continuous analyte sensor.

BRIEF DESCRIPTION OF THE DRAWINGS

Some of the figures shown herein are not necessarily drawn to scale.

DETAILED DESCRIPTION OF THE PREFERRED EMBODIMENT

Figure 1:
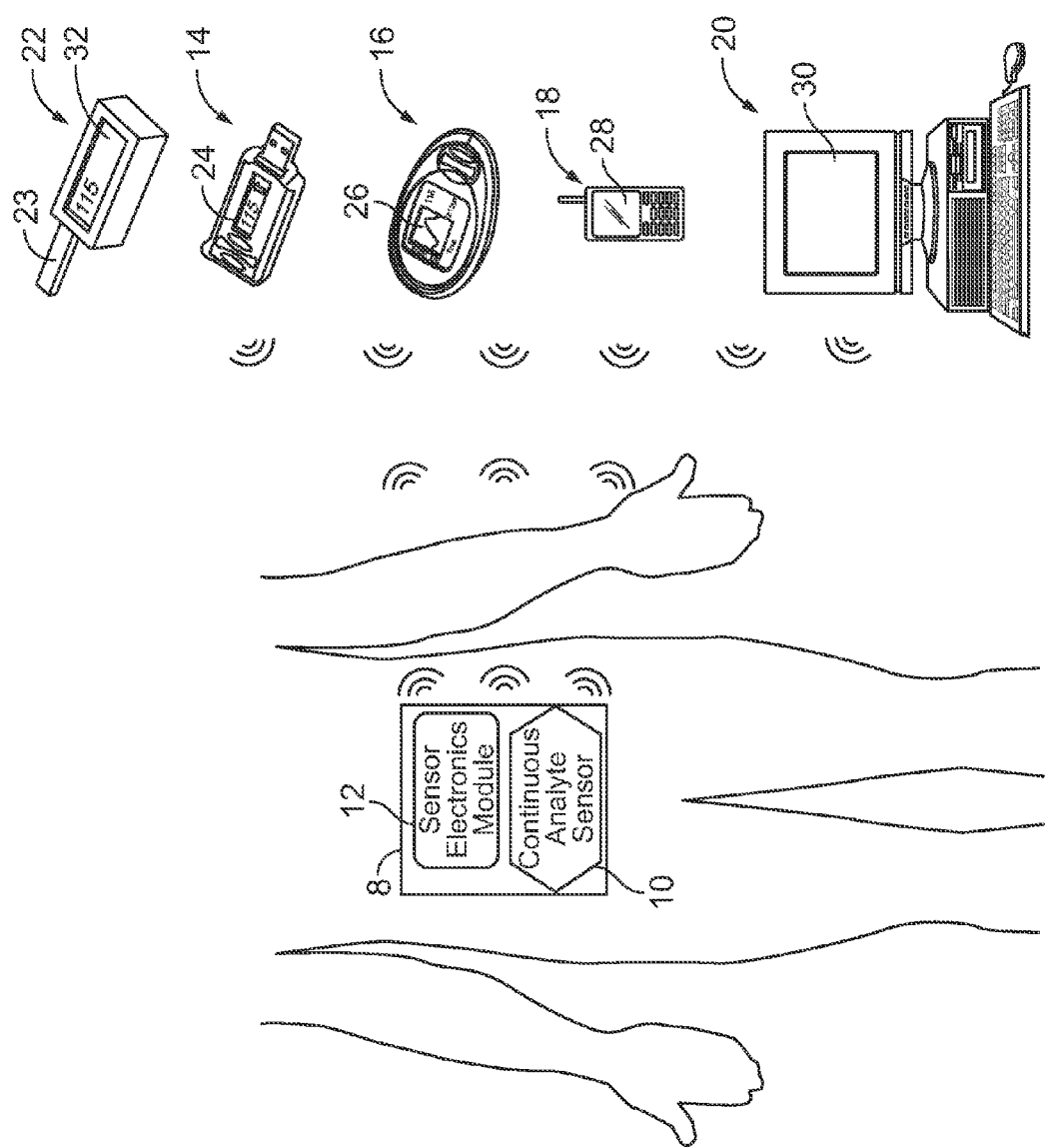
FIG. 1 is a diagram illustrating one embodiment of a continuous analyte sensor system including a sensor electronics module.

The following description and examples describe in detail some exemplary embodiments of sensors, devices, systems, and methods for using the sensors, devices, and systems described herein. There are numerous variations and modifications of the sensors, devices, systems, and methods described herein that are encompassed by the present invention. Accordingly, the description of a certain exemplary embodiment should not be deemed to limit the scope of the present invention.

DEFINITIONS

In order to facilitate an understanding of the preferred embodiments, a number of terms are defined below.

The term "analyte," as used herein, is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products. In some embodiments, the analyte for measurement by the sensing regions, devices, and methods is glucose. However, other analytes are contemplated as well, including, but not limited to: acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli, vesicular stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to: insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The term "continuous," as used herein in reference to analyte sensing, is a broad term, and is to be given its ordinary and customary meaning to a person of ordinary skill in the art (and is not to be limited to a special or customized meaning), and refers without limitation to the continuous, continual, or intermittent (e.g., regular) monitoring of analyte concentration, such as, for example, performing a measurement about every 1 to 10 minutes.

The terms "membrane," "membrane system," or "sensing membrane," as used herein, are broad terms and are used in their ordinary sense, including, without limitation, a permeable or semi-permeable membrane that can be comprised of two or more domains and is typically constructed of materials of a few microns thickness or more, which are permeable to oxygen and are optionally permeable to glucose. In one example, the membrane comprises an immobilized glucose oxidase enzyme, which enables an electrochemical reaction to occur to measure a concentration of glucose.

The term "host," as used herein, is a broad term and is used in its ordinary sense, including, without limitation, mammals such as humans.

The term "electroactive surface," as used herein, is a broad term, and is to be given its ordinary and customary meaning to a person of ordinary skill in the art (and is not to be limited to a special or customized meaning), and refers without limitation to the surface of an electrode where an electrochemical reaction is to take place. As one example, in a working electrode, $H_2O_2$ (hydrogen peroxide) produced by an enzyme-catalyzed reaction of an analyte being detected reacts and thereby creates a measurable electric current. For example, in the detection of glucose, glucose oxidase produces $H_2O_2$ as a byproduct. The $H_2O_2$ reacts with the surface of the working electrode to produce two protons ($2H^+$), two electrons ($2e^-$), and one molecule of oxygen ($O_2$), which produces the electric current being detected. In the case of the counter electrode, a reducible species, for example, $O_2$ is reduced at the electrode surface in order to balance the current being generated by the working electrode.

The term "sensing region," as used herein, is a broad term, and is to be given its ordinary and customary meaning to a person of ordinary skill in the art (and is not to be limited to a special or customized meaning), and refers without limitation to the region of a monitoring device responsible for the detection of a particular analyte.

The term "alarm," as used herein, is a broad term, and is to be given its ordinary and customary meaning to a person of ordinary skill in the art (and is not to be limited to a special or customized meaning), and refers without limitation to an alert or signal, such as an audible, visual, or tactile signal, triggered in response to one or more alarm conditions. In one embodiment, hyperglycemic and hypoglycemic alarms are triggered when present or predicted clinical danger is assessed based on continuous analyte data.

Overview

FIG. 1 is a block diagram of a system that includes a continuous analyte sensor 10 coupled to sensor electronics 12 provided in or on an analyte measuring module 8 configured for on-body mounting to a host. The module 8 continuously measures analyte concentration in a host and provides a data stream that in one embodiment is representative of the host's analyte concentration. Additionally or alternatively, in another embodiment, the data stream may include data that is representative of the rate of change of the host's analyte concentration.

The continuous analyte sensor 10 measures a concentration of an analyte (e.g., glucose) or a species (e.g., hydrogen peroxide or oxygen) indicative of the concentration or presence of the analyte. In some embodiments, the continuous analyte sensor is an invasive, minimally-invasive, or non-invasive device, for example a subcutaneous, transcutaneous, or intravascular device. In some embodiments, the device can analyze a plurality of intermittent biological samples. The continuous analyte sensor can use any method of analyte-measurement (e.g., glucose-measurement), including enzymatic, chemical, physical, electrochemical, spectrophotometric, polarimetric, calorimetric, radiometric, or the like. In alternative embodiments, the continuous analyte sensor can be any sensor capable of determining the concentration level of an analyte in the body, for example oxygen, lactase, hormones, cholesterol, medicaments, viruses, or the like.

The continuous analyte sensor may use any known method to provide an output signal indicative of the concentration of the analyte. The output signal is typically a data stream that is used to provide a value of the measured analyte concentration or the measured rate of change of the analyte concentration. One exemplary embodiment utilizes a subcutaneous glucose sensor as the continuous analyte sensor. However, the sensors, devices, systems, and methods described herein can be applied to any continuous analyte sensor capable of continually or continuously detecting a concentration of analyte of interest and providing an output signal that represents the concentration of that analyte.

Figure 2A:
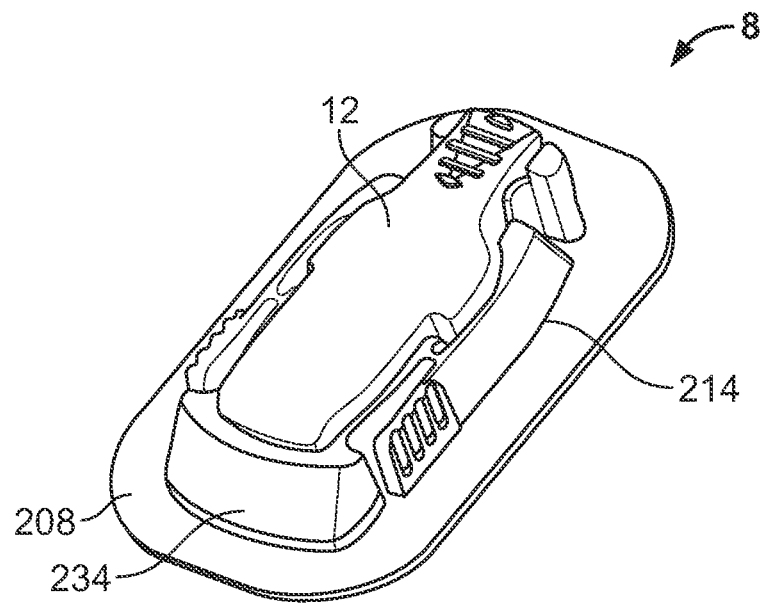
FIG. 2A is a perspective view of a sensor system including a mounting unit and sensor electronics module attached thereto according to one embodiment.
Figure 2B:
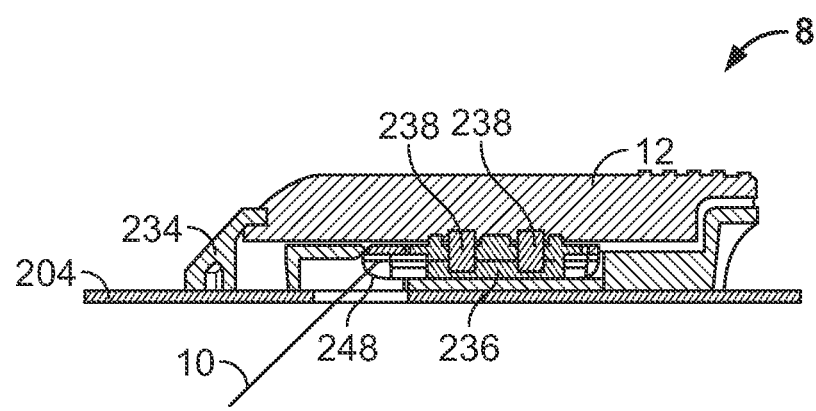
FIG. 2B is a side view of the sensor system of FIG. 2B.

FIGS. 2A and 2B are perspective and side views of a sensor module 8 including a mounting unit 214 and sensor electronics module 12 attached thereto in one embodiment, shown in its functional position, including a mounting unit and a sensor electronics module matingly engaged therein. In some embodiments, the mounting unit 214, also referred to as a housing or sensor pod, comprises a base 234 adapted for fastening to a host's skin. The base can be formed from a variety of hard or soft materials, and can comprises a low profile for minimizing protrusion of the device from the host during use. In some embodiments, the base 234 is formed at least partially from a flexible material, which is believed to provide numerous advantages over conventional transcutaneous sensors, which, unfortunately, can suffer from motion-related artifacts associated with the host's movement when the host is using the device. The mounting unit 214 and/or sensor electronics module 12 can be located over the sensor insertion site to protect the site and/or provide a minimal footprint (utilization of surface area of the host's skin).

In some embodiments, a detachable connection between the mounting unit 214 and sensor electronics module 12 is provided, which enables improved manufacturability, namely, the relatively inexpensive mounting unit 214 can be disposed of when replacing the sensor system after its usable life, while the relatively more expensive sensor electronics module 12 can be reusable with multiple sensor systems. In some embodiments, the sensor electronics module 12 is configured with signal processing (programming), for example, configured to filter, calibrate and/or other algorithms useful for calibration and/or display of sensor information. However, an integral (non-detachable) sensor electronics module can be configured.

In some embodiments, the contacts 238 are mounted on or in a subassembly hereinafter referred to as a contact subassembly 236 configured to fit within the base 234 of the mounting unit 214 and a hinge 248 that allows the contact subassembly 236 to pivot between a first position (for insertion) and a second position (for use) relative to the mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 238 are formed from a conductive elastomeric material, such as a carbon black elastomer, through which the sensor 10 extends.

In certain embodiments, the mounting unit 214 is provided with an adhesive pad 208, disposed on the mounting unit's back surface and includes a releasable backing layer. Thus, removing the backing layer and pressing the base portion 234 of the mounting unit onto the host's skin adheres the mounting unit 214 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Referring back to FIG. 1, the sensor module 8 is in data communication with typically one, but possibly more than 1 recording device 14, 16, 18, 20, 22. These devices may be configured to receive and record at least some of the data stream representative of the hosts's analyte concentration produced and transmitted by the sensor module 8. The recording device 14, 16, 18, 20, 22 may be configured to perform real-time processing and calibration of the data received by the sensor module 8. This may be termed "prospective" processing, as it allows immediate feedback and an ability to prompt the user to take some action in response to current levels of analyte concentration. Predictions of analyte concentration in the near future can also be made based on analysis and processing of current and recent past data received by the recording device 14, 16, 18, 20, 22. It will be appreciated that such prospective processing can be partially or fully performed in the sensor module 8 if desired, and may in general be distributed in any suitable manner throughout the components of the system. As will be discussed further below, these devices 14, 16, 18, 20, 22 typically incorporate displays 24, 26, 28, 30, and 32 respectively.

In some embodiments, one such device is a small (e.g., key fob) recording device 14 that is configured to record at least some of the sensor information, and may be configurable to display information such as an analyte concentration value and a trend arrow. In general, a key fob device is a small hardware device sized to fit on a key chain. Although in some embodiments such a recording device may be formed as or be incorporated into a wrist band, a hang tag, a belt, a necklace, a pendent, a piece of jewelry, an adhesive patch, a pager, an identification (ID) card, and the like, all of which are included by the phrase "small recording device" and/or "key fob device" herein.

In some embodiments, the recording device is a hand-held display device 16 configured to record sensor information including an analyte concentration. Such a device may be configurable to display a graphical representation of the analyte concentration over time such as a previous 1, 3, 5, 6, 9, 12, 18, or 24-hours of sensor data. In some embodiments, the hand-held device 16 is configurable to display a trend graph or other graphical representation, a numeric value, an arrow, and/or to alarm the host. U.S. Patent Publication No. 2005/0203360, which is incorporated herein by reference in its entirety, describes and illustrates some examples of display of data on a hand-held recording device.

In some embodiments, a mobile phone or PDA 18 is configured to operate as a recording device. An application program may be provided on or downloaded to the device 18 to configure it to receive and record sensor information from the sensor module 8. With an appropriate application program, the mobile phone or PDA 18 may be configured to provide display of sensor data and alarm in manner similar to the hand-held device 16.

In some embodiments, a recording device is personal computer (PC) 20 configured to record sensor information. The PC 20 may have software installed, wherein the software enables recording, and/or display, and/or performs data analysis (retrospective processing) of the historic sensor information. In some embodiments, a hardware device can be provided (not shown), wherein the hardware device (e.g., dongle/adapter) is configured to plug into a port on the PC to enable wireless communication between the sensor electronics module 8 and the PC 20.

Another common component of an analyte measuring and monitoring system is a single point analyte monitor (which may be referred to as a BGM device). One example of a recording device including a single point analyte monitor is denoted 22 in FIG. 1. With these devices, the user may obtain a blood sample by pricking their finger, and place the sample on a test strip 23 which is inserted into the single point monitor 22. The single point monitor analyzes colorimetric or other properties of the test strip to derive a blood analyte concentration. Prior to the development and commercialization of continuous measuring systems (which may be referred to as CGM systems), single point monitors 22 were the sole method available for a diabetic to monitor and control glucose levels. This required many unpleasant finger pricks in a day for a patient to control glucose levels properly. Single point monitors 22 are still used in conjunction with CGM systems for calibration purposes and to provide an additional check on continuous system data. The number of single point tests that need to be done in a day, however, is drastically reduced when a CGM system is also used.

In some embodiments, a single point monitor 22 includes the communication and recording functionality of the other recording devices 14, 16, 18, and 20 described above. In other embodiments, single point analyte measurement functionality of single point monitor 22 can be incorporated into the recording devices 14, 16, 18, 20 described above. In either case, a device 14, 16, 18, 20, 22 can provide the functions both a BGM device and CGM recorder in a single device. In one embodiment, a common housing integrates a single point analyte monitor (416 in FIGS. 3 and 4) and device electronics useful for receiving, processing, and displaying continuous analyte data from module 8. Such a device may measure and record single point analyte monitor data and receive, process, and record continuous analyte sensor data. The processing may include calibration of the continuous sensor data using the single point monitor data. In some embodiments, the communication, recording, and processing circuitry is not in the same housing as the single point monitor, but they are in communication with one another with a wired or wireless connection. It will be appreciated that it is somewhat arbitrary whether a device is described as a BGM device with CGM functionality, or a CGM device with BGM functionality. For description purposes herein, all devices with CGM functionality are referred to as recording devices, which devices may also include BGM functionality.

In some embodiments, a recording device is an on-body device that is splittable from, releasably attached to, and/or dockable to the sensor housing (mounting unit, sensor pod, or the like). In some embodiments, release of the on-body recording device turns the sensor off; in other embodiments, the sensor housing comprises sufficient sensor electronics to maintain sensor operation even when the on-body recording device is released from the sensor housing.

It is contemplated that in some embodiments, wireless transmissions may allow for communication not only between one or more recording devices 14, 16, 18, 20, 22 and one continuous analyte sensor module 8, but for communication between one or more recording devices 14, 16, 18, 20, 22 and a plurality of sensor modules, so that a recording device can receive a plurality of data streams from a plurality of sensor modules 8.

Any of the recording devices 14, 16, 18, 20, 22 can be configured to provide alerts or alarms to the host under certain defined measurement and operating conditions. Each alert may be based on one or more alert conditions that indicate when the respective alert should be triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

Each of the alerts may be associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor module.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system may be configured to wait a predetermined amount of time and re-analyze the possibility of avoiding the clinical risk. In some embodiments, when there is a possibility of avoiding the clinical risk, the system may be further configured to provide targets, therapy recommendations, or other information that can aid the patient in proactively avoiding the clinical risk.

Such a system can be configured to operate in a more flexible and useful manner than has previously been performed by such systems. In some embodiments, the system may include an operational mode that prevents the display of CGM data in real-time. This "blinding" of analyte concentration values associated with CGM data may be advantageous for certain diabetics whose doctors believe that real-time CGM data display is not appropriate. In some cases, a physician may use a CGM system with a patient where the patient does not have access to the data for the period of time that the sensor module 8 is installed. Instead, the recording device 14, 16, 18, 20, 22 stores the data for later downloading, further processing, and viewing by the physician to make recommendations or diagnoses for the patient. This later processing and review of previously acquired data may be termed "retrospective" processing as it is useful provide advice on future behavior, but does not provide any information regarding current analyte levels. Conventionally, in such a system no prospective processing or alarm functionality is utilized.

This conventional method of blinded analyte monitoring fails to take advantage of all the capabilities of a CGM system. In some embodiments, therefore, even when operating in a blinded mode, the CGM functionality of the system can be utilized to perform other useful functions without displaying data from the sensor module 8 to the user. The additional features provided by incorporation of CGM technology may include, for example, prospective processing of the analyte data and configurable alarms that may warn a patient of a pending hyperglycemic or hypoglycemic event and configurable, intelligent alerts that prompt the patient to perform a single point analyte measurement (e.g., a blood glucose measurement) at certain times that are determined to be optimal by the device electronics. In a blinded mode, the recorder 14, 16, 18, 20 may be configured to display analyte concentration values measured by the single point analyte monitor. It may also be configured to prospectively process analyte data, and trigger alarms based on the prospective processing, but not display any analyte concentration values associated with the data stream transmitted from the continuous analyte sensor 110.

In some embodiments, a single recording device 14, 16, 18, 20, 22 is capable of operating in both a blinded mode, in which only analyte concentration values measured by the single point analyte monitor are displayed while the continuous data is prospectively calibrated and processed, and an unblinded mode, in which analyte concentration values measured by both the continuous analyte sensor and the single point analyte monitor are displayed. In the blinded mode, the device may be used as a diagnostic tool (e.g., by a physician to determine whether a patient is a diabetic). Furthermore, the blinded mode may also provide the physician with a tool for determining necessary basal adjustments and for obtaining a baseline of a patient's glycemic control. In the unblinded mode, the patient can learn from watching glucose concentration trends throughout the day. For example, in the unblinded mode, the device may provide the patient with a tool to achieve certain diabetes goals, such as, achieving A1c targets without adding hypoglycemia, reducing hypoglycemia, and reducing glucose variability. In either mode, data from the continuous analyte sensor is still recorded, and this data may be subsequently utilized for retrospective processing and analysis.

Figure 3:
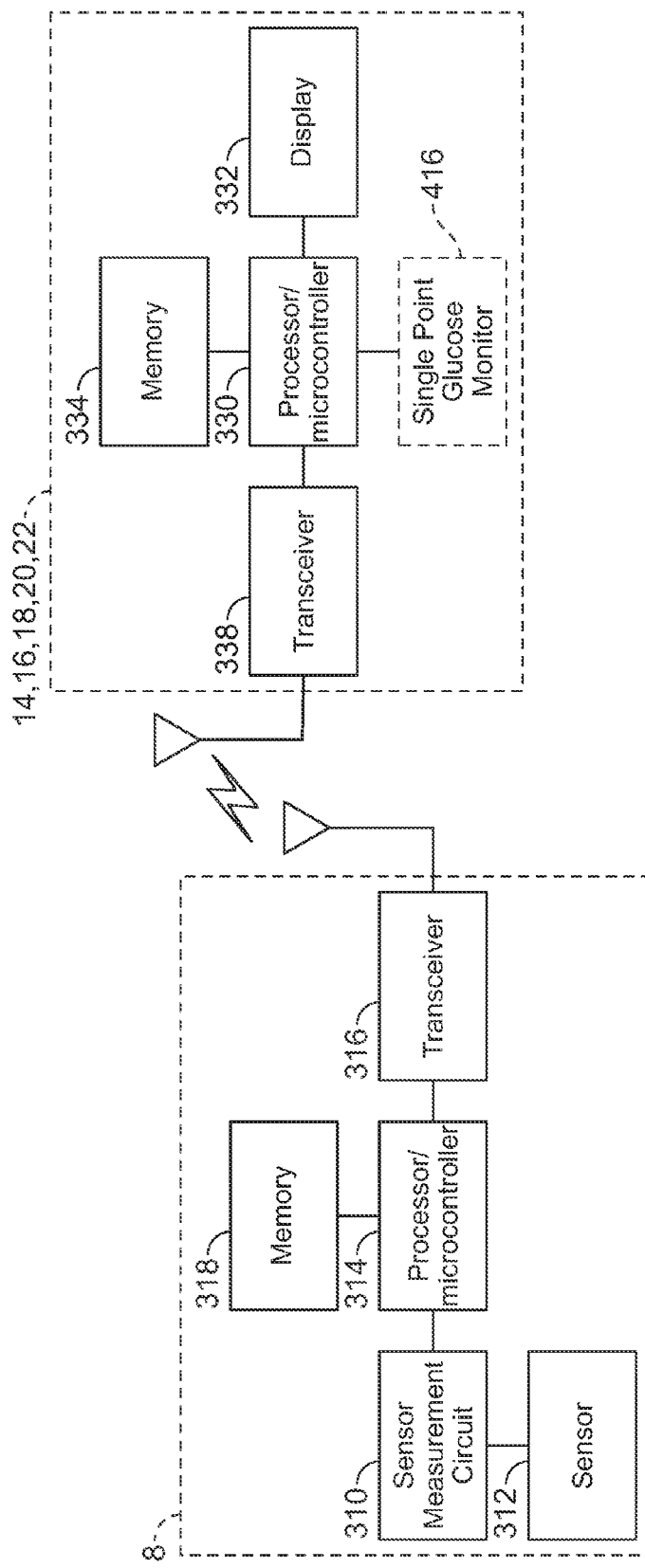
FIG. 3 is an exemplary block diagram illustrating various elements of one embodiment of a continuous analyte sensor system and display device.

FIG. 3 is an exemplary block diagram illustrating various elements of one embodiment of a sensor module 8 and recording device 14, 16, 18, 20, 22. The sensor module 8 may include a sensor 312 (also designated 10 in FIG. 1) coupled to a sensor measurement circuit 310 for processing and managing sensor data. The sensor measurement circuit 310 may be coupled to a processor 314 (part of item 12 in FIG. 1). In some embodiments, the processor 314 may perform part or all of the functions of the sensor measurement circuit 310 for obtaining and processing sensor measurement values from the sensor 312. The processor may be further coupled to a transceiver 316 (part of item 12 in FIG. 1) for sending sensor data and receiving requests and commands from an external device, such as the recording device 14, 16, 18, 20, 22. The sensor module 8 may further include a memory 318 (part of item 12 in FIG. 1) for storing and tracking sensor data.

The recording device 14, 16, 18, 20, 22 may be used for alerting and providing sensor information to a user, and may include a processor 330 for processing and managing sensor data. The display device 14, 16, 18, 20, 22 may include a display 332 and a memory 334 for displaying, storing and tracking sensor data respectively. The display device 14, 16, 18, 20, 22 may further include a transceiver 338 for receiving sensor data and for sending requests, instructions, and data to the sensor module 8. As described above, the recording device 14, 16, 18, 20, 22 may incorporate a single point analyte monitor 416 that is in communication with the processor 330.

The electronics associated with some embodiments of a recording device 14, 16, 18, 20, 22 are described in more detail below with reference to FIG. 4. In one embodiment, analyte (e.g., glucose) from a biological sample produces a current flow at a working electrode of the device 120, with equal current provided by a counter electrode in a reference circuit. The current is converted in an analog section by a current to voltage converter to a voltage, which is inverted, level-shifted, and delivered to an A/D converter in the processor (see FIG. 4). As part of the calibration, the processor can set the analog gain via its control port. The A/D converter is preferably activated at one-second intervals. The processor looks at the converter output with any number of pattern recognition algorithms known to those skilled in the art until an analyte peak is identified. A timer is then activated for about 30 seconds at the end of which time the difference between the first and last electrode current values is calculated. This difference is then divided by the value stored in the memory during instrument calibration and is then multiplied by the calibration analyte concentration. The result includes a calibrated analyte concentration value that is meaningful to a user, and useful in calibrating the data stream from the continuous analyte sensor 110, for example.

Figure 4:
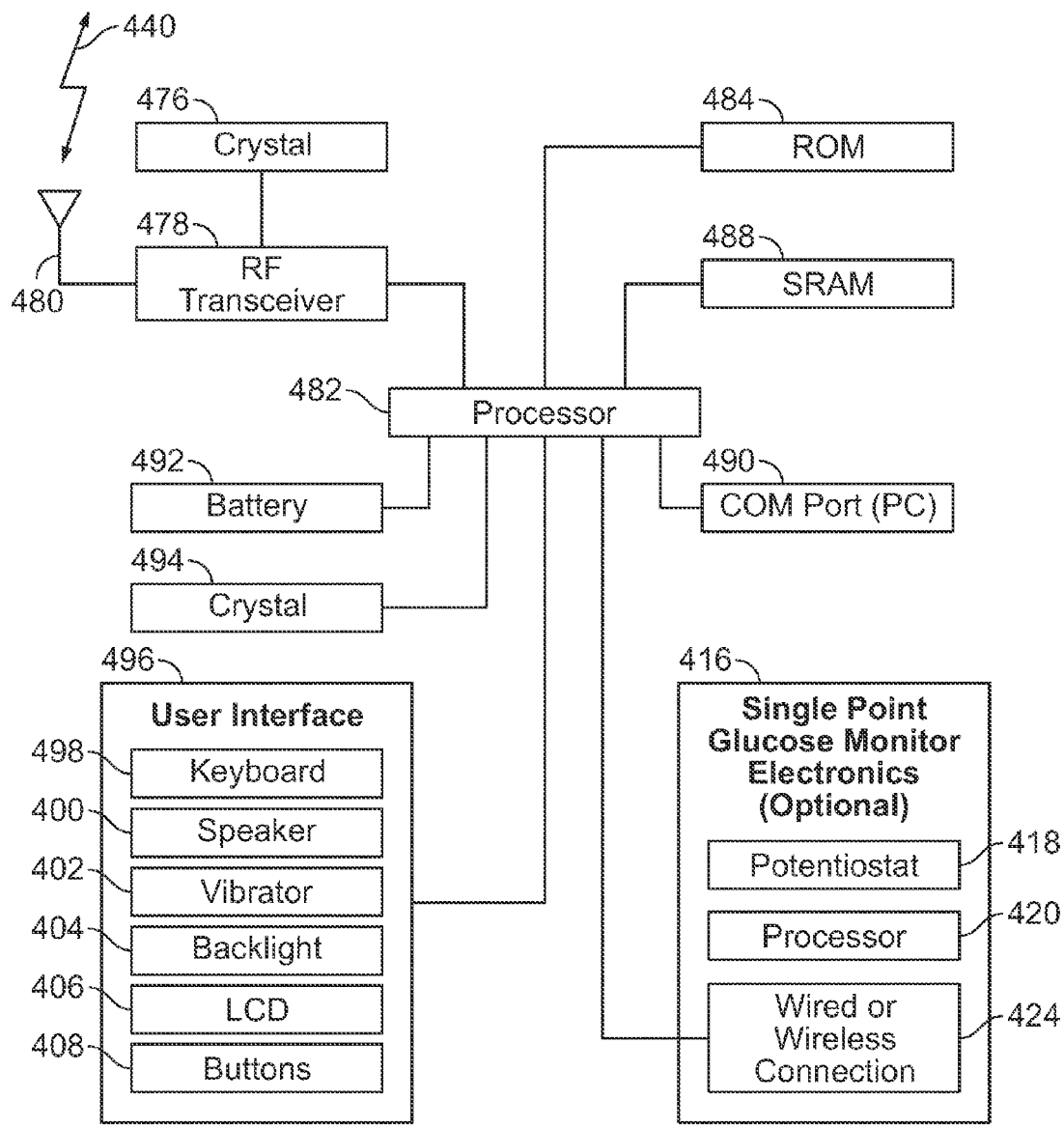
FIG. 4 is a block diagram illustrating one embodiment of the device electronics.

FIG. 4 is a block diagram that illustrates device electronics 150 in one embodiment. A quartz crystal 476 is operably connected to an RF transceiver 478, which together function to receive and synchronize data streams 440 via an antenna 480 (for example, transmission 440 from the RF transceiver 478) from a continuous analyte sensor. Once received, a processor 482 processes the signals, such as described below.

In one embodiment, the processor 482 is the central control unit that provides the processing, such as storing data, analyzing continuous analyte sensor data stream, analyzing single point analyte values, accuracy checking, checking clinical acceptability, calibrating sensor data, downloading data, and controlling the user interface by providing prompts, messages, warnings and alarms, or the like. The ROM 484 is operably connected to the processor 482 and provides semi-permanent storage of data, storing data such as device ID and programming to process data streams (for example, programming for performing calibration and other algorithms described elsewhere herein). SRAM 488 is used for the system's cache memory and is helpful in data processing. For example, the SRAM stores information from the continuous analyte sensor and the single point analyte monitor for later recall by the user or a doctor; a user or doctor can transcribe the stored information at a later time to determine compliance with the medical regimen or a comparison of analyte concentration to medication administration (for example, this can be accomplished by downloading the information through the pc com port 490). In addition, the SRAM 488 can also store updated program instructions and/or patient specific information. In some alternative embodiments, memory storage components comparable to ROM and SRAM can be used instead of or in addition to the preferred hardware, such as dynamic RAM, non-static RAM, rewritable ROMs, flash memory, or the like.

A battery 492 is operably connected to the processor 482 and provides power for the device. In one embodiment, the battery is a standard AAA alkaline battery, however any appropriately sized and powered battery can be used. In some embodiments, a plurality of batteries can be used to power the system. In some embodiments, a power port (not shown) is provided permit recharging of rechargeable batteries. A quartz crystal 494 is operably connected to the processor 482 and maintains system time for the computer system as a whole.

A PC communication (com) port 490 can be provided to enable communication with systems, for example, a serial communications port, USB connector, or the like, which allows for communicating with another computer system (for example, PC, PDA, phone, server, or the like). In one exemplary embodiment, the device is able to download historical data to a physician's PC for retrospective analysis by the physician. The PC communication port 490 can also be used to interface with other medical devices, for example pacemakers, implanted analyte sensor patches, infusion devices, telemetry devices, or the like.

Electronics associated with the single point analyte monitor 416 are operably connected to the processor 482 via a wired or wireless connection 424. The electronics include a potentiostat 418 in one embodiment that measures a current flow produced at the working electrode of the single point analyte monitor 416 when a biological sample is placed on the sensing membrane. The current may then converted into an analog signal by a current to voltage converter, which can be inverted, level-shifted, and sent to an A/D converter. The processor 420 can set the analog gain via its control port (not shown). The A/D converter is preferably activated at one-second intervals. The processor 420 looks at the converter output with any number of pattern recognition algorithms known to those skilled in the art until an analyte peak is identified. A timer is then preferably activated for about 30 seconds at the end of which time the difference between the first and last electrode current values is calculated. This difference is then divided by the value stored in the memory during instrument calibration and is then multiplied by the calibration analyte concentration. The analyte value in milligram per deciliter, millimoles per liter, or the like, is then stored in the processor, displayed on the user interface, used to calibrate of the analyte sensor data stream, downloaded, etc.

In one embodiment, the user interface 496 comprises a keyboard 498, speaker 400, vibrator 402, backlight 402, liquid crystal display (LCD) 406, and one or more buttons 408. The components that comprise the user interface 496 provide controls to interact with the user. The keyboard 498 can allow, for example, input of user information about an individual, such as mealtime, exercise, insulin administration, and reference analyte values. The speaker 400 can provide, for example, audible signals or alerts for conditions such as present and/or predicted hyper- and hypoglycemic conditions. The vibrator 402 can provide, for example, tactile signals or alerts for reasons such as described with reference to the speaker, above. The backlight 404 can be provided, for example, to aid the user in reading the LCD in low light conditions. The LCD 406 can be provided, for example, to provide the user with visual data output. In some embodiments, the LCD is a touch-activated screen. The buttons 408 can provide for toggle, menu selection, option selection, mode selection, and reset, for example. In some alternative embodiments, a microphone can be provided to allow for voice-activated control.

As described elsewhere herein, in some embodiments, determination as to when to trigger a configurable alarm, alert, or prompt may be based at least in part on information associated with the data stream from the continuous analyte sensor. Configurable alarms can mitigate costs by protecting patients against potentially dangerous low and high glucose excursions and possible hospitalization. In some embodiments, one or more alerts are associated with the device electronics. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g., an alert may be based on sensor data from both a glucose sensor and a temperature sensor). For example, a hypoglycemic alert may include alert conditions indicating a minimally required trend in the host's glucose level that has to be present before triggering the alert. The term "trend," as used herein, refers generally to data indicating some attribute of data that is acquired over time, e.g., calibrated or filtered data from a continuous glucose sensor. A trend may indicate amplitude, rate of change, acceleration, direction, etc., of data, such as sensor data, including transformed or raw sensor data.

In one embodiment, each of the alerts is associated with one or more actions that are to be performed in response to triggering of the alert. Alert actions may include, for example, activating an alarm, such as displaying information on the user display of the device or activating audible or vibratory alarm coupled to the device.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include use of dynamic and intelligent estimative algorithms based at least in part on data collected from the continuous analyte sensor, such as, analyte concentration value, rate of change of concentration, rate of acceleration of concentration, etc., thereby providing more appropriate, clinically safe, and patient-friendly alarms. Other information, such as, clinical risk, statistical probabilities, known physiological constraints, time of day, mealtime information, exercise information, insulin administration information, and/or individual historical patterns, and the like, may also be used for determining clinical risk alerts. U.S. Patent Publication No. US-2007-0208246-A1, which is incorporated herein by reference in its entirety, describes some systems and methods associated with the clinical risk alerts (or alarms) described herein. In some embodiments, in response to the clinical risk alerts, prompts or messages can be displayed on the user interface 496 to inform the user about certain procedures, such as "perform another fingerstick measurement." Furthermore, the analyte concentration value measured by the single point analyte monitor can be individually displayed.

In some embodiments, alarms, alerts, or prompts of the device may be activated based on an estimation algorithm that can extrapolate or estimate values for a future time period, such as described in U.S. Patent Publication No. US-2005-0203360-A1, which is incorporated herein by reference in its entirety. For example, the device electronics may be configured to estimate glucose concentration values for an upcoming 15-minute time period. If a potential hypoglycemic or hyperglycemic event is estimated or forecasted based on the estimation algorithm, the device may be configured to warn the patient (e.g., through an alarm or alert) of the present or upcoming event and prompt the patient to take a certain recommended action (e.g., administer insulin).

The sensor data collected from the continuous analyte sensor may be processed prospectively, retrospectively, or both. Prospective processing of sensor data may involve matching sensor data from the continuous analyte monitor with reference glucose values from the single point analyte monitor, such as described in U.S. Pat. No. 7,778,680, which is incorporated herein by reference in its entirety. With retrospective processing of sensor data collected from the continuous analyte sensor and/or the single point analyte monitor are stored in a memory of the device for retrospective analysis. For instance, via the PC communication port 490, the stored data can be transferred or downloaded to another device (e.g., a device, such as a computer, compatible multiple data management systems such as DexCom Data Manager, Diasend, or the like) so that retrospective data analysis may be performed. In some embodiments, the device electronics or a computer, which has received sensor data from the device, compares sensor data from two different analysis time periods (e.g., a first time period during which the device was in a blinded mode and a second time period during which the device was a in an unblinded mode). A performance report is then prepared that discloses changes in sensor data over the various time periods. The performance report may include one or more performance reports, such as graphs, charts, tables, etc., that include and/or otherwise illustrate the determined performance indicators, which may be displayed on a display device of the host computing device or other display device. Depending on the embodiment, the analysis time periods may be any time period, such as one day, one week, two weeks, three weeks, one month, two months, three months, six months, one year, or any other time period. Thus, the performance report module provides the host with reports that indicate changes in sensor data over various time periods. A more detailed description regarding comparing sensor data from two time periods is described in U.S. patent application Ser. No. 12/770,618, filed on Apr. 29, 2010 and entitled "PERFORMANCE REPORTS ASSOCIATED WITH CONTINUOUS SENSOR DATA FROM MULTIPLE ANALYSIS TIME PERIODS", which is incorporated herein by reference in its entirety In another embodiment, the device may come with a USB connector, or the like, that enables connection with a computer having software for analyzing data (e.g., DexCom Data Manager software). In addition, the device and/or the computer may be adapted for plug-and-play, i.e., automatic downloading of and retrospective analysis of sensor data from the continuous analyte sensor, upon connection of the device to the computer.

Figure 5:
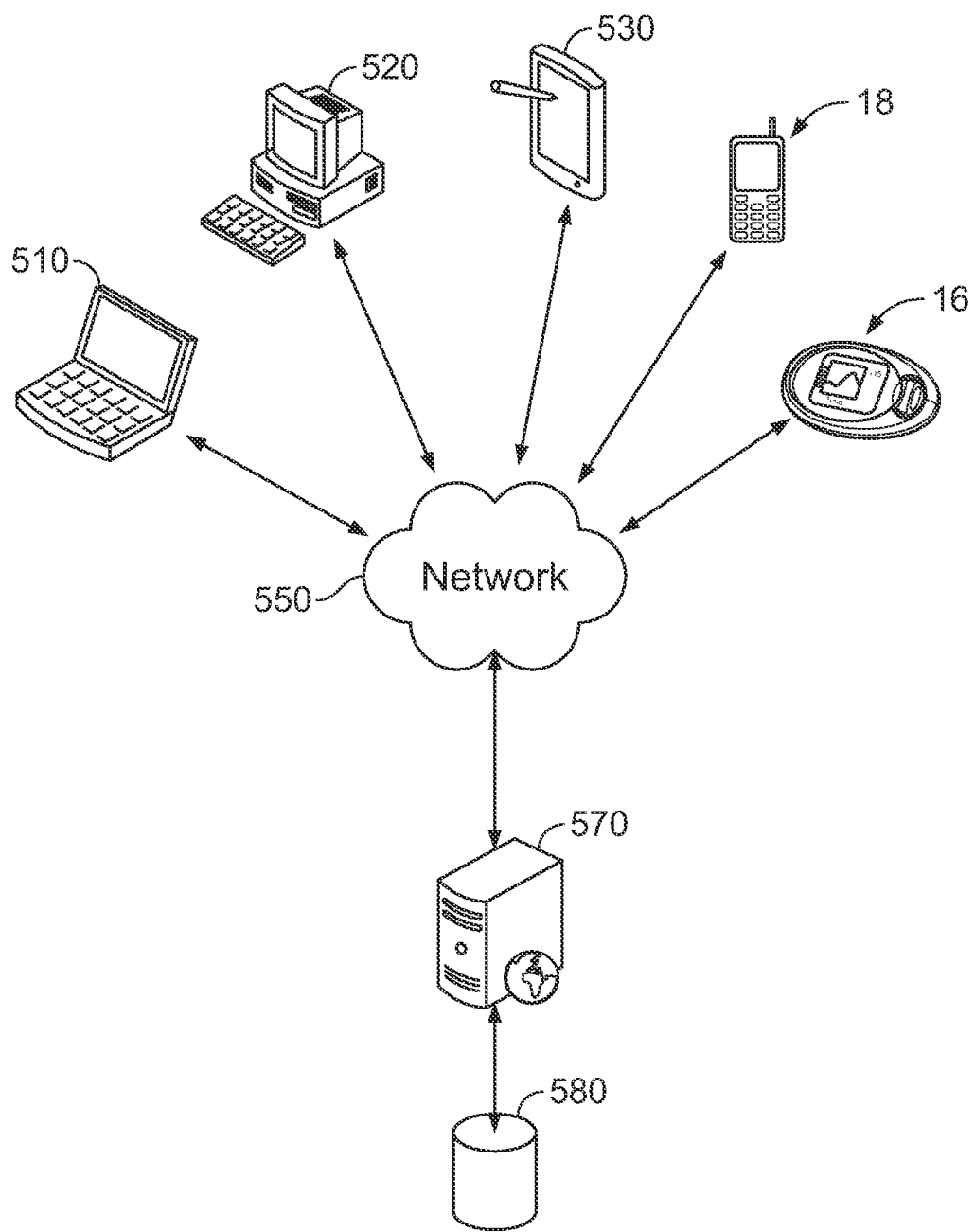
FIG. 5 is a block diagram illustrating a system for storing and retrieving analyte information over a network.

In some embodiments, downloading of CGM data and retrospective analysis may be performed in conjunction with a computer network. Referring to FIG. 5, a block diagram is illustrated of a network on which such a method could be employed. This system operates with a plurality of computers which are coupled together on a network, such as the Internet 550, or other communications network. FIG. 5 depicts a network that includes user computers 510, 520, and 530 that communicate with one or more web servers 570 though communication links that include the Internet 550. The user computers 510, 520, and 530 may be any type of computing device that allows a user to interactively browse the World-Wide-Web, such as a personal computer (PC) that includes a web browser (e.g., Microsoft Internet Explorer™ or Google Chrome™). Suitable user computers equipped with browsers are available in many configurations, including handheld devices (e.g., Apple iPhone™, Google Android, or RIM Blackberry), personal computers (PC), laptop computers, workstations, television set-top devices, tablets, and so forth.

One or more recording devices 14, 16, 18, 20, 22 may also be configured for communication with the network. Connectivity with a wide-area-network such as the Internet may be inherently provided when the recording device is implemented as a mobile phone 18. For other forms of recording device, such as hand-held recording device 16, network communication functionality can be incorporated by including in the device any of a variety of conventional communication circuits normally used in mobile phones and computers with networking capabilities.

In one advantageous embodiment, the recording devices 14, 16, 18, 20, 22 are configured to download CGM data, which may be raw, partially or fully processed, to a web server 570 which may host or otherwise access a database 580 that stores the downloaded CGM data. The web server(s) 570 includes a server computer running a web interface application and capable of selectively delivering data files, such as HTML files, to user computers using a protocol such as HTTP. With this networked CGM data storage, a physician or other caregiver may have access to a patient's CGM data from any device with networked connectivity such as devices 510, 520, and 530. Furthermore, even though the user may not have access to the CGM data due to the system operating in a blinded mode, a physician or other caretaker could have immediate access to the CGM information at any time from any network connected device.

Web server 570 may also dynamically generate content for delivery to user computers in response to a request from a user computer. The content may be generated by web server 570 directly, or may be generated by other computers linked to web server 570 in response to a request from web server 570. Web server 570 may then forward the requested content to a user computer over network 550.

Web server applications may be coded in various programming languages, such as Java, Perl, C#, C, or C++, and are customized to run on their respective servers 570. Web servers 570 may also include applications utilizing a variety of specialized application languages such as Microsoft Silverlight™, or Adobe Flash™ to implement user interfaces displayed on the user computers. These specialized applications may be integrated with files or dynamic content provided by Web server 570 to the user computers in response to a request from those user computers. Web server applications, such as those running on web server 570, may also interface with a database application, such as a SQL Server™ engine from Microsoft Corporation, Oracle™ database engine, or MySQL as part of their architecture. These database applications may control or manage database 580.

Web applications running on web server 570 may access a database of web pages, distributable applications, and other electronic files containing information of various types. Web pages or other electronic files may be viewed on the displays of the user computers by a suitable application program residing on a user computer, such as a browser, or by a distributable application provided to a user computer by the web server 570. It should be appreciated that many different user computers, many different web servers, and many different application servers of various types may be communicating with each other at the same time.

Figure 6:
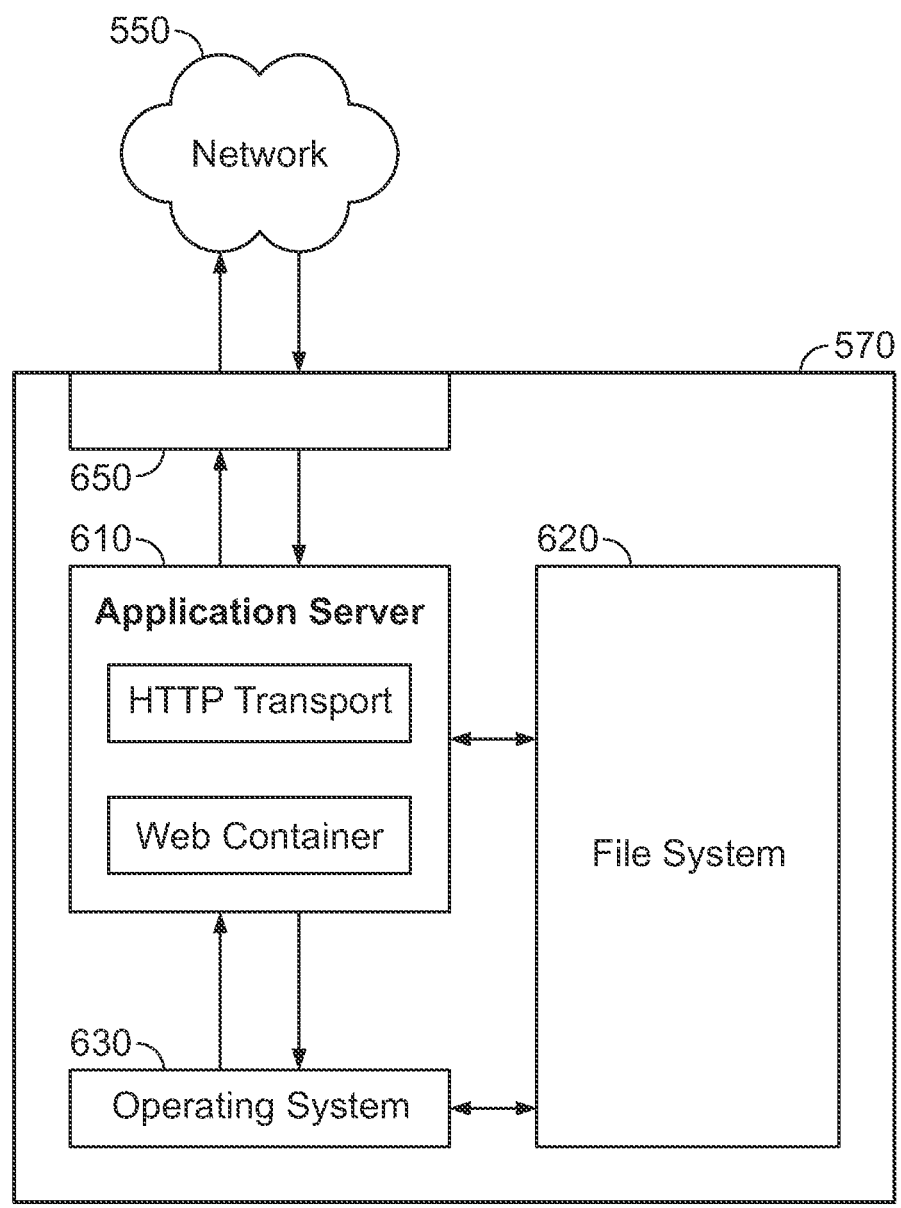
FIG. 6 is a block diagram illustrating a typical architecture of a web server that may implement one of the disclosed operative embodiments.

FIG. 6 is a simplified block diagram illustrating the internal software architecture of one embodiment of web server 570. Web server 570 may be implemented using one of several standard hardware web server platforms including general purpose computers or specialized web server computers from any one of a number of manufacturers to include Hewlett Packard, Apple, Dell, IBM, or the like. These web server hardware platforms may run any one of a number of operating systems 630 to include Microsoft Windows Server, Linux, or several other versions of Unix. Web Server 570 may also be virtualized within a server virtualization system such as VMWare to enable multiple web servers or other applications to operate on one individual computer.

Running on these hardware and operating system web server platforms may be software applications including what is known in the art as an application server 610. Applications servers may include Apache Tomcat, Websphere, or Jboss. Simplified web application architectures may also be used, to include http servers such as an Apache http server running cgi scripts, or open source applications such as Drupal or Jumla.

As illustrated in FIG. 2, Application Server 610 running on web server 570 interacts via a network port 650 with a network 550. Application server 610 may receive requests from the network 150 generated by user computers of FIG. 5 over network port 650. Within Application server 610 may be a web container containing one or more web application programs as described above. These applications may respond to the network requests generated by user computers to deliver web content back to user computers over network 550. These application programs may include instructions that configure a processor running in web server 570 to perform the methods of one or more operative embodiments described herein.

Web server 570 also includes a file system 620. Application server 620 may read and write data to file system 620 in order to respond to requests from user computers over network 550. File system 620 may store static files including html files that define one or more aspects of a user interface provided by Application Server 610 to user computers over network 550. File system 620 may also store instructions of the web applications described above that cause the processor running in web server 570 to perform the method of one or more of the operative embodiments described in this application.

Figure 7:
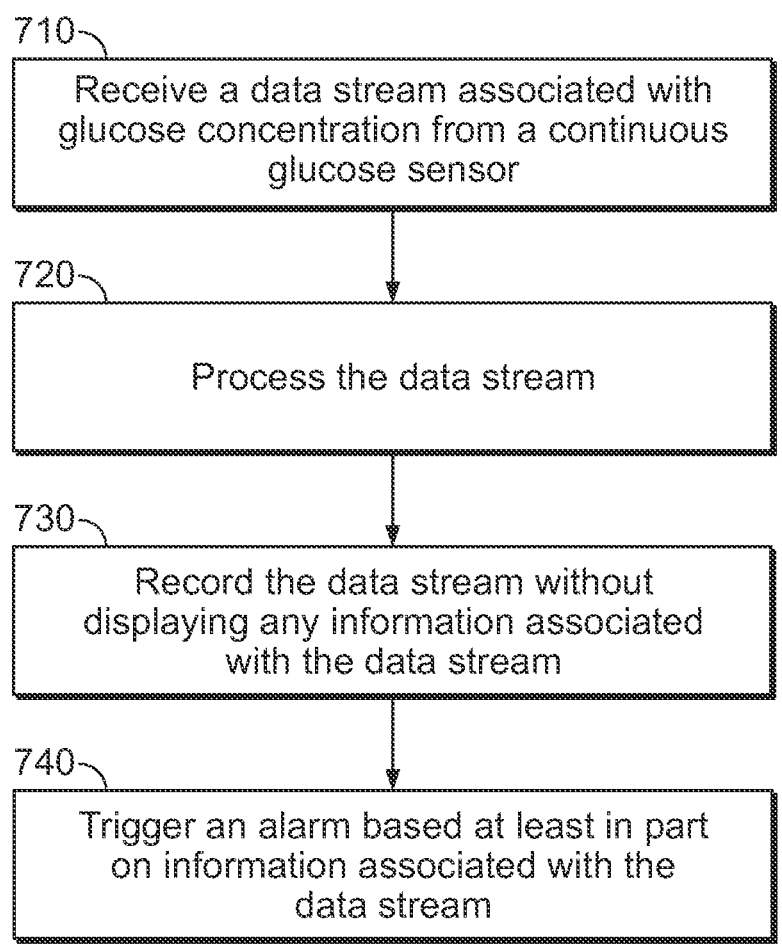
FIG. 7 is a flow chart illustrating a method of operating a continuous analyte monitoring system.

FIG. 7 is a flowchart illustrating a method of operating a continuous analyte monitoring system. This flowchart illustrates an embodiment wherein a continuous glucose monitoring system is used in a blinded mode, but still provides alarms or alerts to a user of the system.

Referring now to FIG. 7, at block 710 a recording device receives a data stream associated with glucose concentration in a host from a continuous glucose sensor. At block 720 the information from the continuous glucose sensor may be processed by the recording device. This processing may include calibration processing, derivations of glucose concentrations, comparing received values or processed values to thresholds, computing trends, etc. At block 730, the recording device stores the data stream and/or processed values derived at least in part from the data stream without displaying any data directly or derived from the data stream to the user of the system. At block 740, an alarm is triggered based at least in part on information associated with the data stream. It will be appreciated that although FIG. 7 is directed to glucose monitoring, the method described can be applied to any analyte.

As described above, a recording device can incorporate or otherwise be in communication with a single point monitor. In some embodiments, the recording device can be configured to display results from the single point monitor even as it hides data from the continuous analyte sensor. In addition, the recording device can be configured to automatically download recorded continuous analyte data to networked storage for access by a physician or other caregiver.

The systems and methods described above have a variety of advantageous features. The recorded device can be configured to hide analyte data from those subjects that a physician determines are better off without having access, yet the recording device can still provide alarms based on the data being recorded using prospective calibration, diagnostics and/or other real-time data processing. Furthermore, the data can be made available essentially immediately over the Internet or other wide-area-network to physicians based on a retrospective analysis that may occur at the recording devices, at the web server or connected device and/or on an application at the a local computer (e.g., web application at a physician's office). Therefore, both prospective and retrospective analysis can be occurring at the same time, with alarm capability immediately available to the host based on the prospective processing, which data for retrospective processing and review is available to the physician or other caregiver at essentially any time.

In some embodiments, a single recording device can be selectively configured to operate in multiple modes. A first mode may be a conventional blinded mode. In this case, the recording device may be configured to display no data or perhaps only data taken from a single point monitor, and may also be configured to provide no alarm functions either. In a second mode, the recording device may operate as a conventional CGM system, where the user has access via the display to glucose values, trend graphs, and other representations of the data being collected by the continuous glucose monitor. This mode may also include configurable alarm functions as is found in current CGM systems. In a third mode, the recording device may restrict user access to the data being collected by the continuous analyte monitor, but still be configured to provide alarm functions to the user of the system.

While various embodiments of the invention have been described above, they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; adjectives such as "known", "normal", "standard", and terms of similar meaning should not be construed as limiting the item described to a given time period or to an item available as of a given time, but instead should be read to encompass known, normal, or standard technologies that may be available or known now or at any time in the future; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A system for monitoring glucose concentration, the system comprising:
   a continuous glucose sensor, the continuous glucose sensor configured to continuously measure glucose concentration and output a data stream associated with glucose concentration; and
   a mobile device configured to:
      operatively connect with the continuous glucose sensor;
      receive the data stream from the continuous glucose sensor;
      process the data stream from the continuous glucose sensor; and
      further receive user input indicative of calibration information via a user interface; wherein the mobile device performs the reception and the processing of the data stream while operating in a blinded mode that prevents display of the data stream associated with the continuous glucose sensor, but enables display of the calibration information via the user interface.

2. The system of claim 1, wherein the mobile device is configured to display glucose concentration values associated with the data stream from the continuous glucose sensor and the calibration information via the user interface while operating in an unblinded mode.

3. The system of claim 2, wherein the mobile device is configured for toggling between the blinded mode and the unblinded mode.

4. The system of claim 1, wherein the mobile device includes at least one processor is configured to determine when to trigger an alarm, wherein the determination of when to trigger the alarm is based at least in part on information associated with the processed data stream.

5. The system of claim 4, wherein the alarm is configured to warn a user of a pending hyperglycemic event or a pending hypoglycemic event.

6. The system of claim 1, wherein the mobile device is configured to determine when to prompt a user to perform calibration to provide the calibration information, and wherein the determination of when to prompt the user is based at least in part on information associated with the processed data stream.

7. The system of claim 1, wherein the continuous glucose sensor is an implantable device.

8. The system of claim 1, wherein the calibration information is a single point glucose measurement.

9. The system of claim 8, wherein the mobile device further comprises a memory for recording the data stream from the continuous analyte sensor and the single point glucose measurement received from a single point glucose monitor.

10. The system of claim 1, wherein the mobile device is configured to upload data from the continuous analyte sensor to networked storage.

11. A method for monitoring a glucose concentration in a user using a mobile computing device, the method comprising:
   receiving, by a mobile device, a data stream indicative of glucose concentration of a host from a continuous glucose sensor;
   processing the data stream by the mobile device;
   further receiving, by the mobile device, user input indicative of calibration information via a user interface; wherein the receiving and the processing of the data stream are performed while the mobile device is operating in a blinded mode that prevents display of the data stream associated with the continuous glucose sensor, but enables display of the calibration information via the user interface.

12. The method of claim 11, further comprising operating in an unblinded mode by the mobile device that allows displaying of the glucose concentration values associated with the data stream from the continuous glucose sensor.

13. The method of claim 12, further comprising toggling between the blinded and the unblinded mode.

14. The method of claim 11, further comprising determining by the mobile device when to trigger an alarm, wherein the determination of when to trigger the alarm is based at least in part on information associated with the processed data stream.

15. The method of claim 14, wherein the alarm is configured to warn a user of a pending hyperglycemic event or a pending hypoglycemic event.

16. The method of claim 11, further comprising determining by the mobile device when to prompt a user to perform calibration to provide the calibration information, wherein the determination of when to prompt the user is based at least in part on information associated with the processed data stream.

17. The method of claim 11, further comprising uploading data from the continuous analyte sensor to network storage.

18. A device for monitoring a glucose concentration of a host measured by a continuous glucose sensor, the device comprising:
   one or more processors; and
   a storage medium configured to store non-transitory computer-readable instructions that, when executed by the one or more processors, cause the device to:
      receive, from a continuous glucose sensor, a data stream indicative of glucose concentration of a host;
      process the data stream; and
      further receive user input indicative of calibration information via a user interface; wherein the reception and the processing of the data stream are performed while the device is operating in a blinded mode that prevents display of the data stream associated with the continuous glucose sensor, but enables display of the calibration information via the user interface.

19. The device of claim 18, wherein the instructions when executed by the one or more processors further causes the device to determine when to trigger an alarm, wherein the determination of when to trigger the alarm is based at least in part on information associated with the processed data stream.

20. The device of claim 18, wherein the instructions when executed by the one or more processors further causes the device to determine when to prompt a user to perform calibration to provide the calibration information, and wherein the determination of when to prompt the user is based at least in part on information associated with the processed data stream.

\* \* \* \* \*

UNITED STATES PATENT AND TRADEMARK OFFICE
CERTIFICATE OF CORRECTION

PATENT NO. : 9,585,608 B2  Page 1 of 1
APPLICATION NO. : 14/938712
DATED : March 7, 2017
INVENTOR(S) : Jorge Valdes et al.

It is certified that error appears in the above-identified patent and that said Letters Patent is hereby corrected as shown below:

In the Specification

In Column 4 at Line 54, Change "andrenostenedione;" to --androstenedione;--.

In Column 5 at Line 3, Change "diptheria/tetanus" to --diphtheria/tetanus--.

In Column 5 at Line 10 (approx.), Change "perioxidase;" to --peroxidase;--.

In Column 5 at Line 24, Change "duodenalisa," to --duodenalis,--.

In Column 5 at Line 32, Change "Trepenoma pallidium," to --Treponema pallidum,--.

In Column 5 at Line 33, Change "stomatis" to --stomatitis--.

In Column 5 at Line 53, Change "Sandrex," to --Sandtex,--.

In Column 5 at Line 54, Change "(barbituates," to --(barbiturates,--.

In Column 16 at Line 16, After "entirety" insert --.--.

In Column 17 at Line 58, Change "Jumla." to --Joomla.--.

In Column 18 at Line 56, Change "the a" to --the--.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*